United States Patent [19]

Ueno et al.

[11] Patent Number: 5,468,880
[45] Date of Patent: Nov. 21, 1995

[54] METHOD OF PRODUCING α, β-UNSATURATED KETONES

[75] Inventors: Ryuji Ueno; Tomio Oda, both of Hyogo, Japan

[73] Assignee: Kabushiki Kaisha Ueno Seiyaku Oyo Kenkyujo, Osaka, Japan

[21] Appl. No.: 244,566

[22] Filed: May 31, 1994

[30] Foreign Application Priority Data

Sep. 30, 1992 [JP] Japan ................................. 4-261283

[51] Int. Cl.⁶ ................................. C07D 305/00
[52] U.S. Cl. ................. 549/263; 549/305; 549/421; 560/126; 568/379; 568/380
[58] Field of Search .................... 560/126; 568/379, 568/380; 549/263, 305, 421

[56] References Cited

U.S. PATENT DOCUMENTS 4,032,576  6/1977  Nelson .......................... 260/586 R

FOREIGN PATENT DOCUMENTS 507625  10/1992  European Pat. Off. .
2655004  6/1978  Germany .
32055  2/1990  Japan .
187637  7/1992  Japan .
01936  3/1989  WIPO .

OTHER PUBLICATIONS

CA 83(5) 42915w 1975.

Primary Examiner—C. Warren Ivy
Assistant Examiner—Amelia Owens
Attorney, Agent, or Firm—Sughrue, Mion, Zinn, Macpeak & Seas

[57] ABSTRACT

Improvement in the technique of synthesizing prostaglandins, particularly those having at least one halogen atom at the 16- or 17-position, which comprises introducing a ω chain into the aldehyde thereby to enable considerable yield improvement in the production of α,β-unsaturated ketones, and which does not involve hydrogen generation and can insure safe operation.

A method of producing α,β-unsaturated ketones by reacting aldehyde with 2-oxoalkyl phosphonate, wherein the reaction was carried out under the presence of a base and a zinc compound.

4 Claims, No Drawings

METHOD OF PRODUCING α, β-UNSATURATED KETONES

This application is a 371 of PCT/JP93/01387 filed Sep. 29, 1993.

DETAILED DESCRIPTION OF THE INVENTION

Field of Industrial Applicability

The present invention relates to a method of producing α,β-unsaturated ketones which are useful as synthetic intermediates for prostaglandins.

Prior Art

It is known that there exist many prostaglandins having the prostanoic acid skeleton represented by the formula:

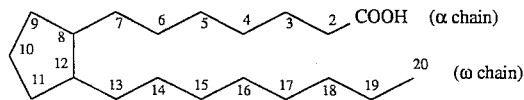

that exhibit characteristic pharmacological activities.

Corey method has been known for long and is still a typical synthetic procedure for producing prostaglandins.

The Corey method includes the step of producing an α,β-unsaturated ketolactone (III) from Corey lactone (I) via Corey aldehyde (II):

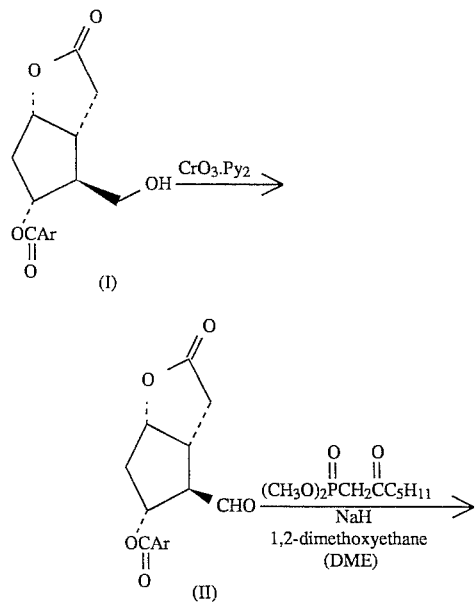

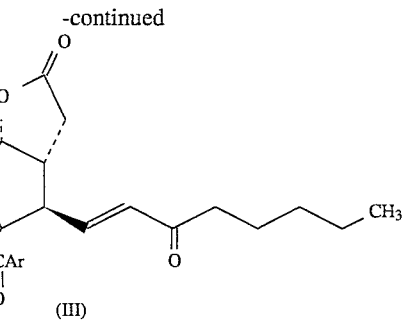

[wherein Ar represents an aromatic group.]

Corey lactone (I) is oxidized to Corey aldehyde (II) using the complex of pyridine and chromium trioxide (so-called Collins oxidation), followed by a reaction between this aldehyde and an anion generated by reacting a dimethyl (2-oxoalkyl)phosphonate with sodium hydride to give the α,β-unsaturated ketolactone (III).

Attempts have been made that reactions are carried out under the presence of sodium hydride and a copper compound, or a thallium compound, to improve the yield. However, the sodium hydride is likely to produce a hydrogen gas, while use of the copper compound does not result in an adequate improvement in the yield. The thallium compound will act to improve the yield to some extent, but this compound is toxic and is very expensive. Thus, it has been desired that further improvement be made in the reaction step.

Task to be Achieved by the Invention

The object of the present invention is to provide a method of producing an α,β-unsaturated ketone in a considerably improved yield in which a ω chain is introduced into the aldehyde during the process of synthesizing prostaglandins, more particularly those having at least one halogen Atom at the 16 or 17 position.

Means for Achieving the Task

Accordingly, the present invention relates to a method of producing an α,β-unsaturated ketone which comprises reacting an aldehyde expressed by the formula:

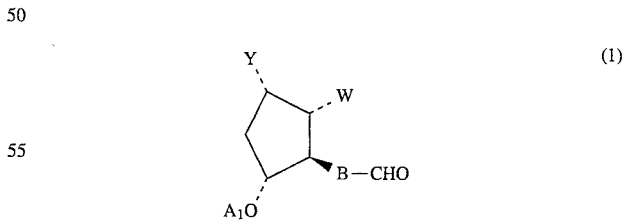

[where, $A_1$ represents a hydrogen atom or a hydroxyl protection group; B represents a simple bond or —$CH_2$—; Y represents —$OA_2$ (in which $A_2$ represents a hydrogen atom or a hydroxyl protection group); W represents —$R_1$—Q (in which $R_1$ represents a bivalent saturated or unsaturated aliphatic hydrocarbon residue having a carbon number of 1 to 10; Q represents a —COOH group or a derivative thereof; or Y and W may combine to form a group expressed by the formula:

(where, $R_1'$ represents a bivalent saturated or unsaturated aliphatic hydrocarbon residue having a carbon number of 1 to 10);
provided that —$OA_1$ and Q may form

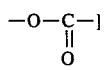

with a 2-oxoalkyl phosphonate expressed by the formula:

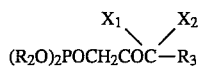 (2)

[where, $X_1$ and $X_2$ represent a hydrogen atom, lower alkyl group or halogen atom; $R_2$ represents a lower alkyl group; $R_3$ represents a saturated or unsaturated aliphatic hydrocarbon group having a carbon number of 1 to 10 which may have a lower alkoxy group, a substituted or unsubstituted cycloalkyl group having a carbon number of 3 to 7, a substituted or unsubstituted phenyl group, or a substituted or unsubstituted phenoxy group; a substituted or unsubstituted cycloalkyl group having a carbon number of 3 to 7; a substituted or unsubstituted phenyl group; or a substituted or unsubstituted phenoxy group], the resulting α,β-unsaturated ketone being expressed by the formula:

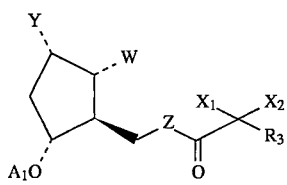 (3)

[where, $A_1$, Y, W, $R_3$, $X_1$ and $X_2$ have same meanings as defined above; and Z represents =CH— or —CH=CH—], the reaction being carried out under the presence of base (exclusive of alkali metal hydrides when $R_1'$ is 1) and a zinc compound.

In the foregoing formula, A embraces all that form a hydroxyl protection group, for example, those expressed by the following formulas:

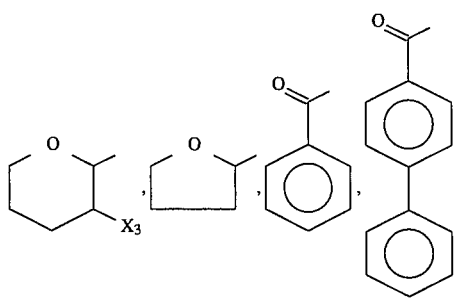

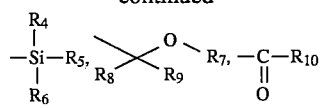

[wherein $X_3$ represents a hydrogen atom or halogen atom; $R_4$, $R_5$, and $R_6$ represent a lower alkyl group or phenyl group; $R_7$ represents a lower alkoxy group or a lower alkyl group which may have a silylgroup; $R_8$ and $R_9$ represent a hydrogen atom or lower alkyl group; and $R_{10}$ represents a lower alkyl group].

The term "aliphatic hydrocarbon" with respect to $R_1$ and $R_3$ means a hydrocarbon having a straight chain or branched chain (provided that the branched chain preferably has a carbon number of 1 to 3). The term "unsaturated" means the state in which inter-carbon atomic bonds of a main chain or side chain include at least one or more than one double bond and/or triple bond in an isolated, separated, or continuous condition. Preferred unsaturated bonds include a double bond at the 2-position, a double bond or triple bond at the 5-position, and a double bond at the 17-position.

The term "halogen" embraces fluorine, chlorine, bromine, and iodine.

The term "lower", unless otherwise specified, embraces groups having a carbon number of 1 to 6.

The term "lower alkyl" embraces straight chain or branched chain hydrocarbon groups having a carbon number of 1 to 6, including, for example, methyl, ethyl, propyl, isopropyl, butyl, isobutyl, t-butyl, pentyl, and hexyl.

The term "lower alkoxy" means lower alkyl-O-.

The term "cycloalkyl" signifies a group resulting from the ring closure of an alkyl group having a carbon number of more than 3. Examples of such group include cyclopropyl, cyclobutyl, cyclopentyl, and cyclohexyl.

Substituent groups for cycloalkyl, phenyl or phenoxy groups having a carbon number of 3 to 7 with respect to $R_3$ include, for example, lower alkyl groups, halogen atoms, and halogenated lower alkyl groups. The terms "lower alkyl group" and "halogen atom" have same meanings as defined hereinabove, and the term "halogenated lower alkyl group" embraces lower alkyl groups having at least one halogen, preferably 1 to 3 halogens. Examples of such halogenated lower alkyl groups include chloromethyl, bromomethyl, fluoromethyl, trifluoromethyl, 1,2-dichloroethyl, chloropropyl, chlorobutyl, chloropentyl, and chlorohexyl.

The term "derivative" with respect to a carboxyl group represented by Q embraces salts (preferably pharmaceutically allowable salts), esters, and amides.

Suitable "pharmaceutically allowable salts" embrace conventional nontoxic salts which include salts resulting from reactions with inorganic bases, for example, alkali metal salts (such as sodium salt and potassium salt), alkali earth metal salts (such as calcium salt and magnesium salt), and ammonium salts; and salts resulting from reactions with organic bases, for example, amine salts (such as methyl amine, dimethyl amine, cyclohexyl amine, benzyl amine, piperidine, ethylene diamine, ethanol amine, diethanol amine, triethanol amine, tris(hydroxymethyl amino)ethane, monoethyl-monoethanol amine, lysine, procaine, and caffeine salts), basic amino acid salts (such as arginine salt and lysine salt), and tetraalkyl ammonium salts. These salts may be produced from corresponding acids and bases, for example, according to conventional procedures or by salt exchange.

Examples of esters include such aliphatic esters as lower alkyl esters, such as methyl ester, ethyl ester, propyl ester, isopropyl ester, butyl ester, isobutyl ester, t-butyl ester, pentyl ester, and 1-cyclopropylethyl ester, lower alkenyl esters, such as vinyl ester and allyl ester, lower alkynyl esters, such as ethynyl ester and propynyl ester, hydroxy (lower) alkyl esters, such as hydroxyethyl ester, and lower alkoxy (lower) alkyl esters, such as methoxymethyl ester and 1-methoxyethyl ester; and aryl (lower) alkyl esters including, for example, aryl esters, benzyl esters, triethyl esters and benzhydryl esters which are substituted as required, such as phenyl ester, tosyl ester, t-butylphenyl ester, salicyl ester, 3,4-dimethoxyphenyl ester, and benzamidephenyl ester. Examples of amides include mono- or di-lower alkyl amides, such as methyl amide, ethyl amide, and dimethyl amide; aryl amides, such as anilide and toluidide; and alkyl or aryl sulfonylamides, such as methyl sulfonylamide, ethyl sulfonylamide, and tolyl sulfonylamide.

The present invention is characterized in that the reaction between aldehyde (1) and 2-oxoalkyl phosphonate (2) to yield an α,β-unsaturated ketone (3) is carried out under the presence of a base and a zinc compound.

By carrying out the reaction under the presence of the base and zinc compound it is possible to achieve considerable improvement in the yield of the α,β-unsaturated ketone over the conventional method in which a base is used alone or any other prior art method. This feature is found most remarkable where the 2-oxoalkyl phosphonate (2) is a 2-oxoalkyl phosphonate useful for the synthesis of prostaglandins having at least one halogen atom at the 16- or 17-position in which at least one of $X_1$ and $X_2$ is a halogen atom, more particularly a fluorine atom.

In the present invention, base may be of the kind which can draw out one of two hydrogen atoms attached to one carbon atom between PO and

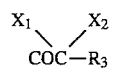

in the 2-oxoalkyl phosphonate (2) and, in effect, anionize the 2-oxoalkyl phosphonate (2).

Examples of bases useful in the conduct of the present invention include alkali hydrides, alkoxides, amides, organic alkalis, sulfinyl carbanion compounds, secondary amines, tertiary amines, aromatic heterocyclic compounds, and alkyl hydroxides.

In regard to alkali hydrides, those expressed by the formula H-M or $H_2$-M [where, M represents an alkali metal or alkali earth metal] may be used, for example. Specifically, sodium hydride, potassium hydride, and calcium hydride are enumerated as such, of which sodium hydride is especially preferred.

Exemplary as useful alkoxides are those expressed by the formula $R_{11}$-O-M or $R_{11}$-O-M-$OR_{12}$ [where, $R_{11}$ and $R_{12}$ represent a lower alkyl group which may have a branched or double bond, a cycloalkyl group having a carbon number of 3 to 7 or phenyl group; and M represents an alkali metal or alkali earth metal]. Specifically, sodium methoxide, sodium ethoxide, potassium t-butoxide; magnesium methoxide, and magnesium ethoxide are enumerated as such, of which potassium t-butoxide is especially preferred.

Exemplary as useful amides are those expressed by the formula:

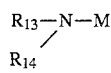

[where, $R_{13}$ and $R_{14}$ represent a hydrogen atom, a lower alkyl group which may have a branched or double bond, a cycloalkyl group having a carbon number of 3 to 7, phenyl group or trimethyl silyl group; and M represents an alkali metal]. Specifically, lithium amide, sodium amide, potassium amide, lithium diisopropyl amide, sodium diisopropyl amide, potassium diisopropyl amide, lithium cyclohexyl isopropyl amide, sodium cyclohexyl isopropyl amide, potassium cyclohexyl isopropyl amide, lithium dicyclohexyl amide, sodium dicyclohexyl amide, potassium dicyclohexyl amide, lithium bis(trimethylsilyl) amide, sodium bis (trimethylsilyl) amide, and potassium bis(trimethylsilyl) amide are enumerated as such, of which sodium amide is especially preferred.

Exemplary as useful organic alkalis are those expressed by the formula $R_{15}$-M or $R_{16}$-M-$R_{17}$ [where, $R_{15}$ and $R_{16}$ represent a lower alkyl group which may have a double or triple bond, a cycloalkyl group having a carbon number of 3 to 7, phenyl group or triphenylmethyl group; $R_{17}$ represents a halogen atom, a lower alkyl group which may have a branched, double, or triple bond, a cycloalkyl group having a carbon number of 3 to 7, phenyl group or triphenylmethyl group; and M represents an alkali metal or alkali earth metal]. Specifically, methyl lithium, n-butyl lithium, s-butyl lithium, t-butyl lithium, and phenyl lithium are enumerated as such, of which t-butyl lithium is especially preferred.

Exemplary as useful sulfinyl carbanions are those expressed by the formula:

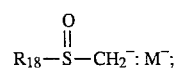

[where, $R_{18}$ represents a lower alkyl group which may have a branched or double bond, a cycloalkyl group having a carbon number of 3 to 7 or phenyl group; and M represents an alkali metal]. Specifically, lithium methylsulfinyl carbanion, sodium methylsulfinyl carbanion, and potassium methylsulfinyl carbanion are enumerated as such, of which sodium methylsulfinyl carbanion is especially preferred.

Exemplary as useful secondary amines are those expressed by the formula:

[where, $R_{19}$ and $R_{20}$ represent an alkyl group having a carbon number of 1 to 10 which may have a branched or double bond, a cycloalkyl group having a carbon number of 3 to 7, phenyl group or trimethylsilyl group. $R_{19}$ and $R_{20}$ may combine to form a ring]. In case that both $R_{19}$ and $R_{20}$ are alkyl groups having a carbon number of 1 to 10 which may have a branched or double bond, they are preferably secondary or tertiary alkyl groups having a carbon number of not less than 3. Specifically, diisopropylamine, cyclohexyl isopropylamine, dicyclohexylamine, bis(trimethylsilyl) amine, and 2,2, 6,6-tetramethyl piperidine are enumerated as such, of which diisopropylamine is especially preferred.

Exemplary as useful tertiary amines are those expressed by the formula:

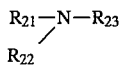

[where, $R_{21}$, $R_{22}$ and $R_{23}$ represent a lower alkyl group which may have a branched or double bond, a cycloalkyl group having a carbon number of 3 to 7 or phenyl group. $R_{21}$ and $R_{22}$ may combine to form a ring]. Specifically, trimethylamine, triethylamine, tripropylamine, tributylamine, diisopropyl ethylamine, phenyl dimethylamine, 1-methylpiperidine, 1-ethylpiperidine, 1-methylpyrrolidine, and 1-ethylpyrrolidine are enumerated as such, of which triethylamine is especially preferred.

Useful as aromatic heterocyclic compounds are pyridine compounds, such as pyridine, lutidine, picoline, collidine, 4-dimethylamino pyridine, quinoline, and isoquinoline; diazine compounds, such as pyrimidine, pyrazine, pyridazine, 1,5-diazabicyclo[4.3.0]non-5-ene, and 1,8-diazabicyclo[5.4.0]undec-7-ene; azole compounds, such as pyrrole, thiazole, and oxazole; and diazole compounds, such as imidazole. Of these, especially preferred are pyridine compounds, which may be expressed, for example, by the formula:

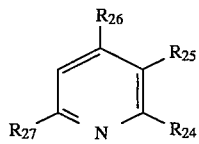

[where, $R_{24}$, $R_{25}$, $R_{26}$ and $R_{27}$ represent a hydrogen atom, a lower alkyl group which may have a branched or double bond (though $R_{24}$ and $R_{25}$, or $R_{25}$ and $R_{26}$, may combine to form an aromatic ring), or

(in which $R_{28}$ and $R_{29}$ represent a hydrogen atom or a lower alkyl group which may have a branched or double bond)].

Exemplary as useful alkali hydroxides are those expressed by the formula HO-M or (HO)$_2$-M [where, M represents an alkali metal or alkali earth metal]. Specifically, lithium hydroxide, sodium hydroxide, potassium hydroxide, calcium hydroxide, strontium hydroxide, and barium hydroxide are enumerated as such, of which sodium hydroxide is especially preferred.

In the present invention, "zinc compound" may be any compound containing a zinc atom. For example, zinc halides, such as zinc chloride and zinc bromide; and organic zincs, such as zinc acetate, are used as such, and in particular zinc halides are preferred.

The amount of the base to be used is preferably about 1 equivalent relative to the amount of the 2-oxoalkyl phosphonate (2), and the amount of the zinc compound is preferably from 0.5 to 1 equivalent relative to the amount of the 2-oxoalkyl phosphonate (2).

Reaction solvents are not particularly specified, for example ethers, such as tetrahydrofuran, dioxane, ethylether, dimethoxyethane, and t-butylmethyl ether, aromatic compounds, such as benzene and toluene, and hydrocarbon halides, such as dichloroethane, are preferable for use as such.

The amount of the reaction solvent is in the range of 1 to 100 ml relative to 1 g of aldehyde (1), preferably in the range of 3 to 80 ml.

The reaction temperature range may be from 0° to 100° C., preferably from 20° to 80° C.

The reaction time may be in the range of 4 to 150 hours, preferably in the range of 4 to 100 hours.

EXAMPLES

Example 1

Synthesis of (1S,5R,6R,7R)-6-[(E)-4,4-difluoro- 3-oxo-5-phenylpento-1-enyl]-7-(tetrahydropyranyloxy)-2-oxybycyclo[3,3,0]octan-3-one:

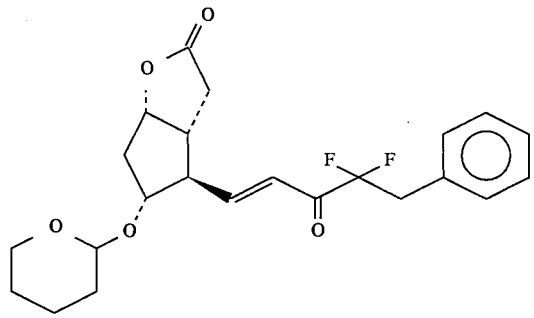

A dichloromethane solution of oxalyl chloride (2-M, 9.38 ml) was added to dichloromethane anhydride (9.4 ml), which was cooled to −78° C. DMSO (2.66 ml) was added dropwise, and agitation was carried out for 10 minutes. A dichloromethane solution (10 ml) of Corey lactone (A) (3.204 g) was then added dropwise with stirring over a period of 1 hour. Triethylamine (6.97 ml) was added with stirring at −40° C. for 1 hour. After a usual work-up, the Corey aldehyde (B) was obtained.

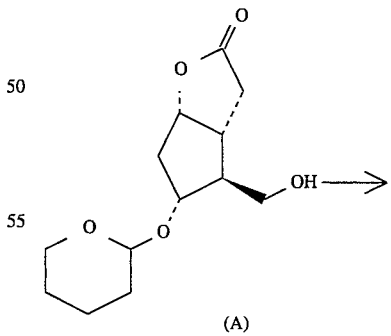

(A)

-continued

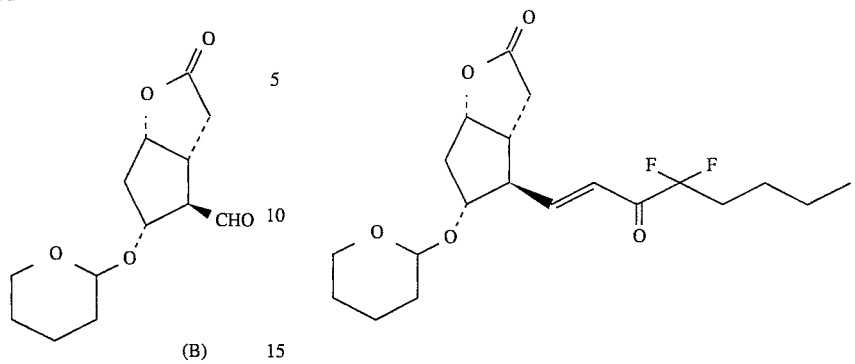

(B)

Yield: 3.292 g

To a THF solution (5 ml) of dimethyl (3,3-difluoro-4-phenyl-2-oxybutyl phosphonate (4.383 g), held at 0° C., was added dropwise t-butoxy potassium (1.0-M THF solution, 15 ml). After being stirred at room temperature for 30 minutes, the mixture was cooled to 0° C., followed by addition of zinc chloride (2.04 g). Stirring was effected again at room temperature for 30 minutes. To the solution was added a THF (5 ml) solution of Corey aldehyde (B) with stirring at room temperature for 15 hours and at 40° C. for 20 hours. The crude product obtained after the usual work-up was chromatographed (silica gel 400 g, ethyl acetate:n-hexane 45:55) and thus (1S,5R,6R,7R)-6-[(E)-4,4-difluoro-3-oxo- 5-phenylpento-1-enyl]-7-tetrahydropyranyloxy-2-oxabicyclo[ 3,3,0]octan-3-one was obtained.

Yield: 2.632 g (50%, 2 steps).

Example 2

Synthesis of (1S,5R,6R,7R)-6-[(E)-4,4-difluoro-3-oxoocto-1-enyl]-7-(tetrahydropyranyloxy)-2-oxabicyclo[3,3,0]octan-3-one:

To a t-butoxy potassium solution (1.0-M THF solution, 174 ml) was added dropwise a THF solution (10 ml) of dimethyl(3,3-difluoro-2-oxoheptyl)phosphonate (45.1 g), and stirring was carried out at room temperature for 30 minutes, followed by addition of zinc chloride (23.8 g). The mixture was agitated for 1 hour and 50 minutes, and then Corey aldehyde (B) (46.0 g) which was obtained in the same way as in Example 1 was added thereto. Then, the resulting mixture was kept in a temperature range of 40° to 45° C. for 20 hours. The crude product obtained after the usual work-up was chromatographed (silica gel 1.8 kg, ethyl acetate:n-hexane 1:2) and thus (1S,5R,6R,7R)-6-[(E)-4,4-difluoro-3-oxoocto- 1-enyl]-7-tetrahydropyranyloxy-2-oxabicyclo[ 3,3,0]octan-3-one was obtained.

Yield: 48.4 g (69%)

Example 3

Synthesis of (1S,5R,6R,7R)-6-[(E)-5,5-difluoro- 8-methoxy-4-oxoocto-2-enyl]-7-(tetrahydropyranyloxy)-2-oxabicyclo[ 3,3,0]octan-3-one:

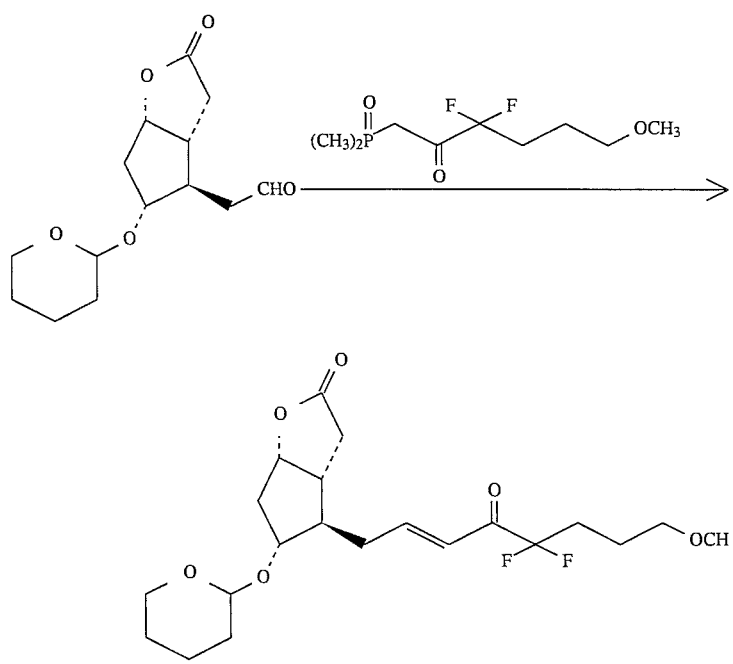

Dimethyl (3,3-difluoro-6-methoxy-2-oxoheptyl) phosphonate (0.0971 g) was dissolved in THF (0.25 ml) in an atmosphere of argon and the solution was kept at 0° C. A THF solution (1.0-M, 0.354 ml) of t-butoxy potassium was added dropwise to the solution, and stirring was carried out at room temperature for 30 minutes, followed by addition of zinc chloroanhydride (0.0443 g) and further stirring for 1 hour. Then, a THF (0.25 ml) solution of (1S,5R,6R,7R)-6-formylmethyl-7-(tetrahydropyranyloxy)- 2-oxabicyclo[3,3,0]octan-3-one (0.0972 g) was added dropwise, and stirring was carried out at room temperature for 30 minutes. A 20-hour stirring at 45° C. followed. Acetic acid (0.02 ml) was added at 0° C., and then the mixture was poured into a cooled aqueous solution of saturated ammonium chloride. Extraction was carried out with ethyl acetate three times. Combined ethyl acetate layers were washed in aqueous saturated sodium bicarbonate and also in saturated salt water, and were they dried. The filtrate was concentrated under reduced pressure, and the resulting crude product was chromatographed on a column of silica gel (ethyl acetate/ hexane=4/6) to yield the (1S,5R,6R,7R)-6-[(E)-5,5-difluoro-8-methoxy-4-oxoocto-2-enyl]- 7-(tetrahydropyranyloxy)-2-oxabicyclo[3,3,0]octan- 3-one, a colorless and oily material.

Yield: 0.0939 g (76.4%)

n. m. r. (CDCl$_3$) δ:1, 4–1.9 (8 H. m), 1.95 3.0 H. m), 3.32 (3 H, s), 3.41 (2 H, t, J=6.1 Hz), 3.35–3.6 (1 H. m), 3.84 (1 1/2 H. m), 4.09 (1/2 H. m), 4.63 (1 H. m), 5.00 (1 H, td, J=12.7 Hz, J=7.6 Hz, J= 3.5 Hz), 6.56 (1 H. m), 7.07–7.23 (1 H, m)

mass m/z: 416 (M)

Example 4

Synthesis of (1S,5R,6R,7R)-6-[(E)-4,4-difluoro-3-oxoocto-1-enyl]-7-(benzoyloxy)-2-oxabicyclo[ 3,3,0]octan-3-one:

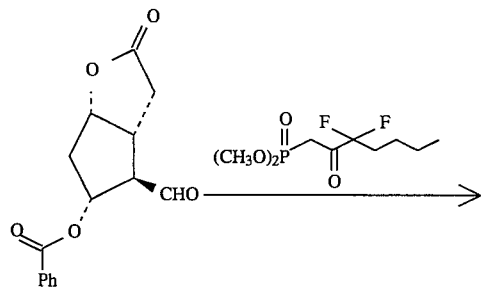

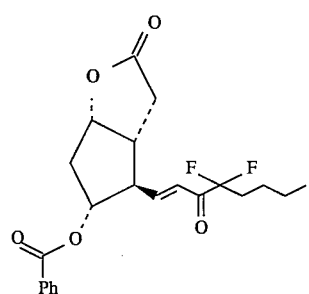

Sodium amide (0.0342 g) was added into a reactor in which the same was kept at 0° C. A THF (2 ml) solution of dimethyl(3,3-difluoro-2-oxoheptyl)phosphonate (0.2259 g) was added and agitation was carried out at room temperature for 45 minutes. The mixture was kept at 0° C. and zinc chloride (0.1133 g) was added thereto with stirring at room temperature for 1 hour. Then, (1S,5R,6R,7R)-6-formyl-7-(benzoyloxy)-2-oxabicyclo[ 3,3,0]octan-3-one (0.200 g) was added in its solid state and stirring was effected at room temperature for 18 hours. A THF (2 ml) solution of phosphonate anions which was prepared from phosphonate (0.2300 g), sodium amide (0.0348 g) and zinc chloride (0.1094 g) was added, and reaction was carried out at room temperature for 4 hours. The crude product obtained after the usual work-up was purified on a column of silica gel (hexane/ethyl acetate=3/2) to yield the subject compound, a colorless solid material.

Yield: 0.2181 g (73.6%)

n. m. r. (CDCl$_3$) δ:0.90 (3H, t, J=7.5 Hz), 1.15–1.55 (4 H. m), 1.85–2.15 (2 H. m), 2.25–2.75 (3 H, m), 2.80–3.10 (3. H, m), 5.14 (1 H, t, J=5 Hz), 5.36 (1 H. m), 6.66 (1 H, d, J=15 Hz), 7.03 (1 H. dd, J= 15 HZ, J=7.5 Hz), 7.40–8.00 (5 H, m)

Example 5

Synthesis of (1S,5R,6R,7R)-6-[(E)-4,4-difluoro-3-oxoocto-1-enyl]-7-(benzoyloxy)-2-oxabicyclo[ 3,3,0]octan-3-one:

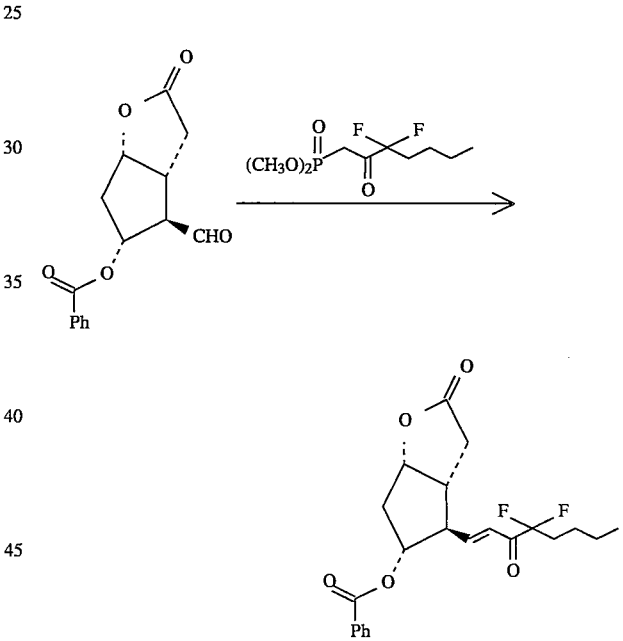

To a THF (2.0 ml) solution of dimethyl(3,3-difluoro-2-oxoheptyl)phosphonate (0.5648 g), which was kept at −100° C. was added dropwise t-butyl lithium (1.7-M pentane solution, 1.16 ml). The temperature was raised to 0° C. and then zinc chloride (0.2685 g) was added, followed by stirring at room temperature for 1 hour. To the mixture was added (1S,5R,6R,7R)-6-formyl-7-(benzoyloxy)- 2-oxabicyclo[3,3,0]octan-3-one (0.2000 g), and then stirring was effected at room temperature for 41 hours. The crude product obtained after the usual work-up was purified on a column of silica gel (hexane/ethyl acetate=3 / 1) to yield the subject compound, a colorless solid material.

Yield: 0.1655 g (55.8%)

Example 6

Synthesis of (1S,5R,6R,7R)-6-[(E)-4,4-difluoro-3-oxoocto-1-enyl]-7-(benzoyloxy)-2-oxabicyclo[ 3,3,0]octan-3-one:

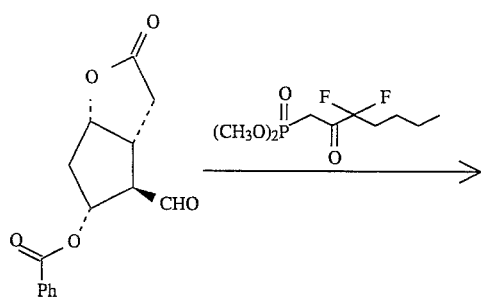

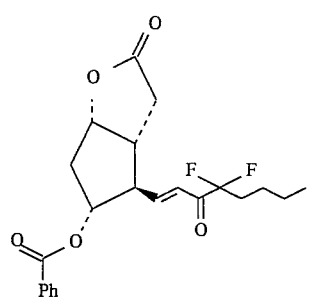

Sodium hydride (60%, 0.0788 g) was washed with pentane, and to this sodium hydride was added DHSO (0.3419 g). The mixture was stirred at 70° C. for 1 hour to give sodium methylsulfinyl carbanion, which was in turn diluted with THF (1 ml) at room temperature. A THF (2 ml) solution of dimethyl(3,3-difluoro-2-oxoheptyl)phosphonate (0.5648 g) was added dropwise and the mixture was stirred at room temperature for 1 hour. Then, zinc chloride (0.2685 g) was added and further stirring was carried out for 1 hour. To the mixture was added (1S,5R,6R,7R)-6-formyl-7-(benzoyloxy)-2-oxabicyclo[ 3,3,0]octan-3-one (0.2000 g), and then stirring was effected at room temperature for 17 hours. The crude product obtained after the usual work-up was purified on a column of silica gel (hexane/ethyl acetate= 3 / 1) to yield the subject compound, a colorless solid material.

Yield: 0.2720 g (91.8%)

Example 7

Synthesis of (1S,5R,6R,7R)-6-[(E)-4,4-difluoro-3-oxoocto-1-enyl]-7-(benzoyloxy)-2-oxabicyclo[ 3,3,0]octan-3-one:

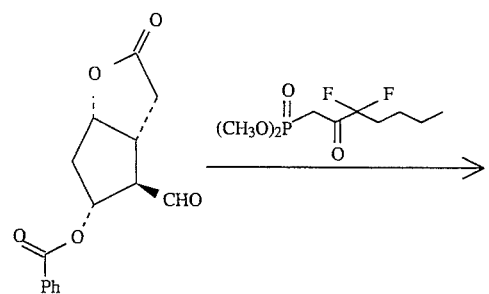

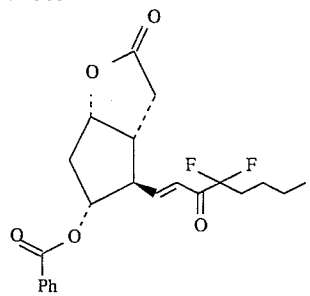

A THF (0.5 ml) solution of diisopropylamine (0.1989 g) was added to a THF (1.5 ml) solution of dimethyl(3,3-difluoro-2-oxoheptyl)phosphonate (0.5650 g), and stirring was carried out at room temperature for 30 minutes. Zinc chloride (0.2668 g) was added to the mixture with stirring effected for 45 minutes. Then, a THF (1.9 ml)solution of (1S,5R,6R,7R)-6-formyl-7-(benzoyloxy)- 2-oxabicyclo[3,3,0]octan-3-one (0.2000 g) was added, and stirring was carried out for 45 hours. The crude product obtained after the usual work-up was purified on a column of silica gel (hexane/ethyl acetate= 3 / 1) to yield the subject compound, a colorless solid material.

Yield: 0.1848 g (62.4%)

Example 8

Synthesis of (1S,5R,6R,7R)-6-[(E)-4,4-difluoro-3-oxoocto-1-enyl]-7-(benzoyloxy)-2oxabicyclo[3,3,0]octan- 3-one:

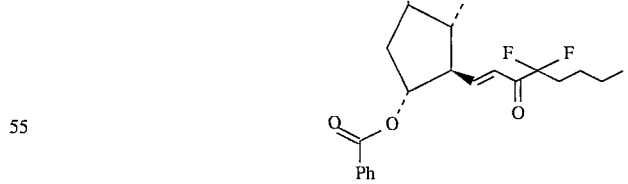

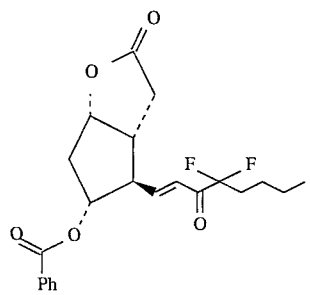

Triethylamine (0.1990 g) was added to a THF (2 ml) solution of dimethyl(3,3-difluoro-2-oxoheptyl) phosphonate (0.5653 g), and the mixture was kept at 65° C. for 30 minutes. The temperature of the mixture was lowered to room temperature, and zinc chloride (0.2657 g) was added with stirring for 30 minutes. A THF (1.7 ml) solution of (1S,5R,6R,7R)-6-formyl-7-(benzoyloxy)-2-oxabicyclo [3,3,0]octan-3-one (0.2003 g) was added, and stirring was carried out at room temperature for 15.5 hours. The crude product obtained after the usual work-up was purified on a column of silica gel (hexane/ethyl acetate=2.5 / 1) to yield the subject compound, a colorless solid material.

Yield: 0.2228 g (75.2%)

Example 9

Synthesis of (1S,5R,6R,7R)-6-[(E)-4,4-difluoro-3-oxoocto-1-enyl]-7-(benzoyloxy)-2-oxabicyclo[ 3,3,0]octan-3-one:

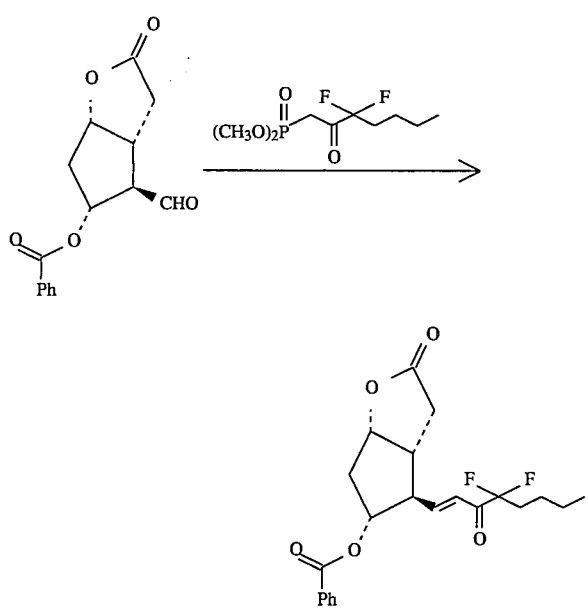

Dimethylamino pyridine (0.2399 g) was added to a THF (2 ml) solution of dimethyl(3,3-difluoro-2-oxoheptyl) phosphonate (0.5654 g), and stirring was carried out at room temperature for 45 minutes. Zinc chloride (0.2688 g) was added with stirring at room temperature for 1 hour. A THF (1.9 ml) solution of (1S,5R,6R,7R)-6-formyl-7-(benzoyloxy)-2-oxabicyclo [3,3,0]octan-3-one (0.2029 g) was added, and stirring was carried out at room temperature for 22 hours. The crude product obtained after the usual work-up was purified on a column of silica gel to yield the subject compound.

Yield: 0.2406 g (81.2%)

Example 10

Synthesis of (1S,5R,6R,7R)-6-[(E)-4,4-difluoro-3-oxoocto-1-enyl]-7-(benzoyloxy)-2-oxabicyclo 3,3,0]octan-3-one:

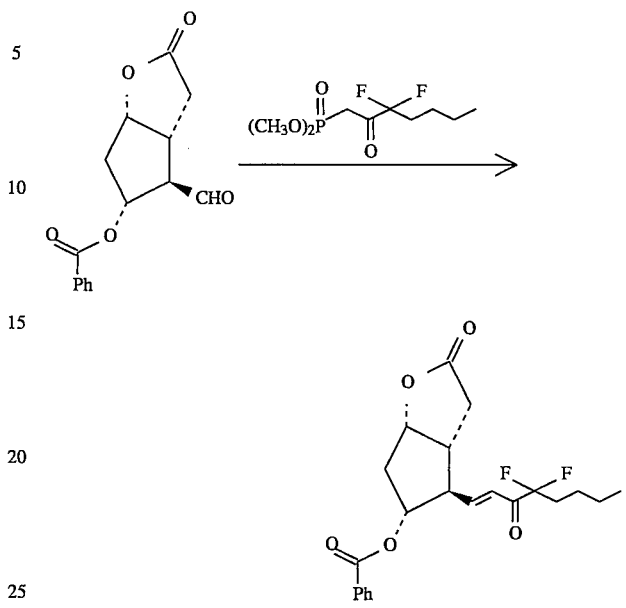

To a THF (2 ml) solution of dimethyl (3,3-difluoro-2-oxoheptyl) phosphonate (0.5648 g), kept at 0° C., was added a 1N-sodium hydroxide solution (1.97 ml). The mixture was stirred at room temperature for 10 minutes and was then concentrated under reduced pressure. To the residue obtained was added toluene (5 ml), and the mixture was concentrated under reduced pressure so that water was azeotropically separated. The resulting colorless crystal was dried under reduced pressure. The dried crystal was dissolved in THF (2 ml), followed by addition of zinc chloride (0.2685 g) and by stirring at room temperature for 1 hour. Then, (1S,5R,6R,7R)-6-formyl- 7-(benzoyloxy)-2-oxabicyclo [3,3,0]octan-3-one (0.2000 g) was added, and stirring was carried out at room temperature for 22 hours. The crude product obtained after the usual work-up was purified on a column of silica gel (hexane / ethyl acetate=3 / 1) to yield the subject compound, a colorless solid material.

Yield: 0.2749 g (92.8%)

Example 11

Synthesis of 7-{(1R,2R,3R,5S)-5-acetoxy-2-[ (E)-4-cyclopentyl-4,4-difluoro-3-oxobuto-1-enyl]-3-(tetrahydropyranyloxy) cyclopentyl} methyl heptanoate:

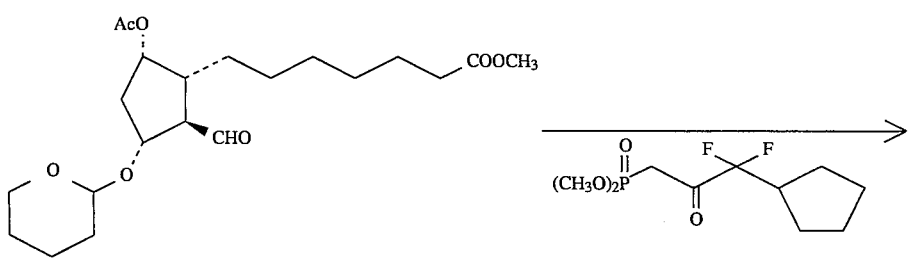

-continued

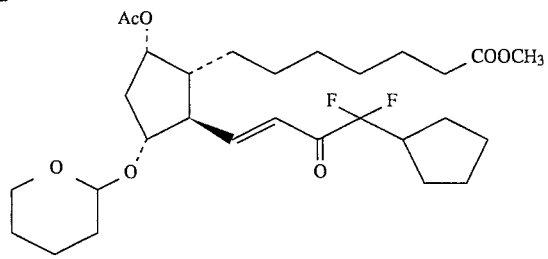

Sodium hydride (60%, 0.400 g) was suspended in dry THF (15 ml), and the suspension was kept at 0° C. A THF nyloxy) cyclopentyl} non-7-isopropyl hydrochloride:

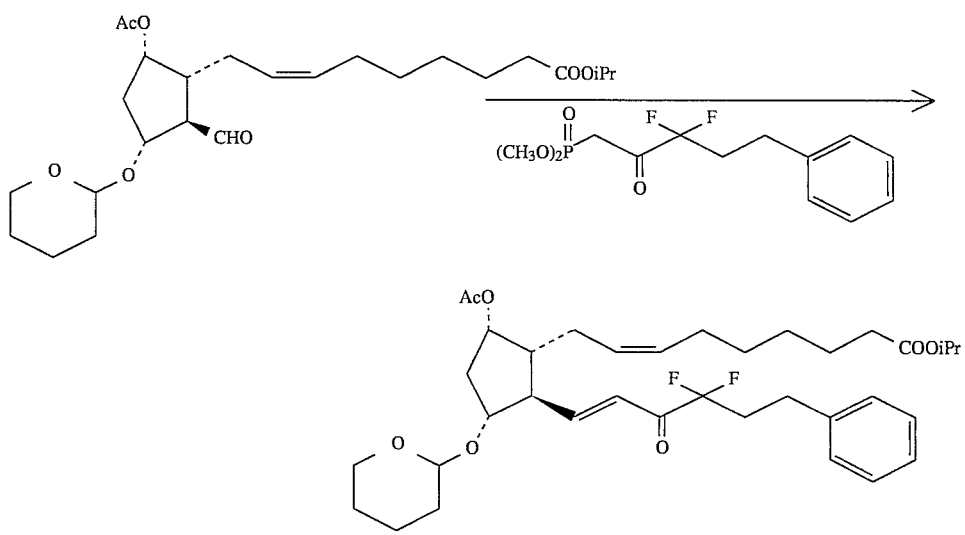

(5 ml) solution of dimethyl (3-cyclopentyl-3,3-difluoro-2-oxopropyl) phosphonate (2.71 g)was added and stirring was carried out for 20 minutes, followed by addition of zinc chloride (0.680 g). After being stirred at room temperature for 30 minutes, the mixture was kept at 0° C. Then, a THF (10 ml) solution of 7-{ (1R,2R,3R,5S)-5-acetoxy-2-formyl-3-(tetrahydropyranyloxy) cyclopentyl} methyl heptanoate (2.00 g) was added. The reaction solution was stirred at room temperature for 17.1/2 hour and at 40° C. for 5.1/2 hours. A THF (7.0 ml) solution of phosphonate anion which was prepared from phosphonate (1.36 g), sodium hydride (0.210 g) and zinc chloride (0.680 g) was added, and reaction was further carried out for 17.1/2 hours. The crude product obtained after the usual work-up was purified on a column of silica gel (hexane / ethyl acetate=3 / 1) to yield the subject compound, an oily material of light yellow color.

Yield: 2.42 g (89.0%)

n. m. r. (CDCl$_3$) δ: 1.0–2.0 (26 H, m), 2.06 (3 H, s), 2.28 (2 H, t, J=7.5 Hz), 2.35–2.85 (3 H, m), 3.41 (1 H, m), 3.63 (3 H, s), 3.5–3.9 (1 H, m), 3.9– 4.2 (1 H, m), 4.49 (1/2 H, m), 4.56 (1/2 H, m), 5.13 (1 H, t, J=5 Hz), 6.62 (1/2 H, d, J=10 Hz), 6.66 (1/2 H, d, J=10 Hz), 7.00 (1/2 H, dt, J=10 Hz, J=10 Hz), 7.08 (1/2 H, dt, J=10 Hz, J=10 Hz)

Example 12

Synthesis of (Z)-9-{(1R,2R,3R,5S)-5-acetoxy-2-[ (E)-4,4-difluoro-3-oxo-6-phenylhexe-1-enyl]-3-(tetrahydropyra- 60% sodium hydride (0.259 g) was suspended in THF (50 ml), and the suspension was kept at 0° C. A THF (10 ml) solution of dimethyl (3,3-difluoro-5-phenyl-2-oxopentyl) phosphonate (2.07 g) was added and stirring was carried out for 20 minutes, followed by addition of zinc chloride (0.852 g) and by further stirring at room temperature for 1 hour. Then, a THF (20 ml) solution of (Z)-9[(1R,2R,3R,5S)-5-acetoxy-2-formyl-3-(tetrahydropyranyloxy) cyclopentyl] non-7-isopropyl hydrochloride was added. The mixture was heated under reflux for 3 days. The crude product obtained after the usual work-up was purified on a column of silica gel (hexane / ethyl acetate=5 / 1) to yield the subject compound, an oily material of light yellow color.

Yield: 1.06 g (74.3%)

n. m. r. (CDCl$_3$) δ: 1.22 (6 H, d, J=6.0 Hz), 1.2–3.0 (24 H, m), 2.07 (3 H, s), 2.24 (2 H, t, J=7.5 Hz), 3.3–3.55 (1 H, m), 3.65–3.95 (1 H, m), 3.95– 4.25 (1 H, m), 4.5–4.6 (1 H, m), 5.00 (1 H, Sept. J= 6.0 Hz), 5.10 (1 H, m), 5.2–5.5 (2 H, m), 6.65 (1/2 H, d, J=10 Hz), 6.73 (1/2 H, d, J=10 Hz), 7.09 (1/2 H, dd, J=10 Hz, J=10 Hz), 7.45 (5.1/2 H, m)

Example 13

Synthesis of (1S,10R,11R,13S)-13-[(E)-5,5-difluoro-4-oxoocto-2-enyl]-11-hydroxy-2-oxabicyclo [8,2, 1]tridece-7(Z)-ene-3-one:

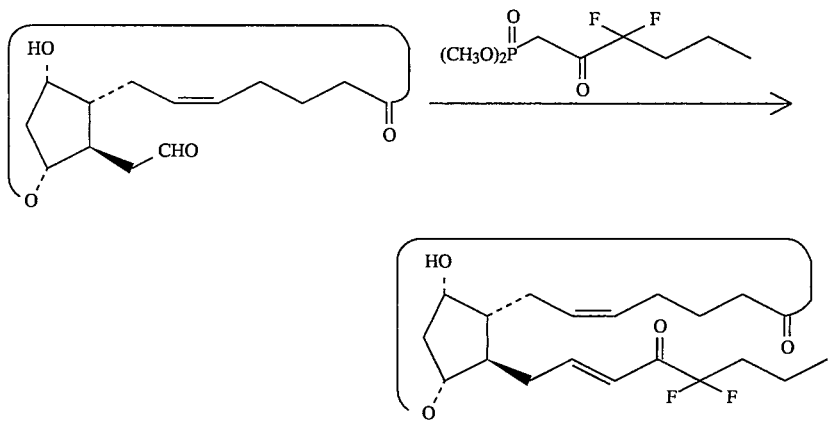

Sodium hydride (60%, 0.160 g) was suspended in dry THF (20 ml), and the suspension was kept at 0° C. A THF (3 ml) solution of dimethyl (3,3-difluoro-2-oxohexyl) phosphonate (0.977 g) was added and stirring was carried out at room temperature for 1 hour, followed by addition of zinc chloride (0.545 g) at 0° C. and by further stirring at room temperature for 2 hours. The mixture was then cooled to 0° C., and a THF (5 ml) solution of (1S,10R,11R,13S)-13-(formylmethyl)-11-hydroxy-2-oxabicyclo [8,2,1]tridece-7(Z)-ene-3-one (0.240 g) was added. The resulting mixture was heated under reflux overnight. The solution was cooled to 0° C. and was added with acetic acid (0.230 g). The crude product obtained after the usual work-up was purified on a column of silica gel (hexane / ethyl acetate=3 / 1) to yield the subject compound, an oily material of light yellow color.

Yield: 0.2390 g (67.8%)

n. m. r. (CDCl$_3$), δ:0.95 (3H, t, J=6.5 Hz), 1.37–1.75 (3 H, m), 1.78–2.75 (16 H, m), 4.56 (2 H, m), 5.12 (1 H, t, J=10 Hz), 5.46 (1 H, m), 6.50 (1 H, d, J=15 Hz), 7.11 (1H, dt, J=15 Hz, J=7.5 Hz)

Example 14

Synthesis of 7-{(1R,2R,3R,5S)-5-acetoxy-2-[ (E)-4-cyclohexyl-4,4-difluoro-3-oxobuto-1-enyl]-3-(tetrahydropyranyloxy) cyclopentyl} isopropyl heptanoate:

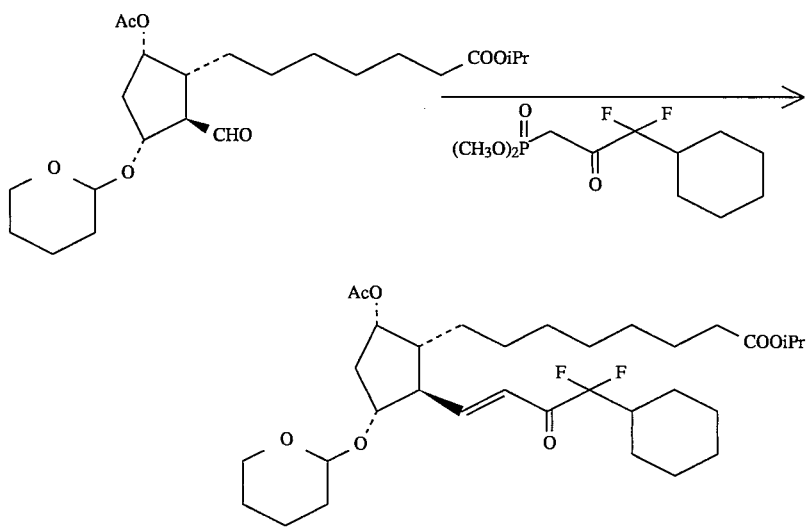

To a THF solution (1M, 12.89 ml) of t-butoxy potassium, kept at 0° C. was added dropwise a THF (18.3 ml) solution of dimethyl(3-cyclohexyl-3,3-difluoro-2-oxopropyl) phosphonate (3.664 g). The mixture was stirred at room temperature for 30 minutes, followed by addition of zinc chloride (1.597 g) and further stirring for 30 minutes. A THF (12.5 ml) solution of 7-[ (1R,2R,3R,5S)-5-acetoxy-2-formyl-3-(tetrahydropyranyloxy) cyclopentyl] isopropyl heptanoate (2.500 g) was added, and the mixture was heated under reflux for 62 hours. The crude product obtained after the usual work-up was purified on a column of silica gel (ethyl acetate / hexane=4 / 1) to yield the subject compound, a colorless oily material.

Yield: 2.831 g (82.6%)

n. m. r. (CDCl$_3$), δ: 1.22 (6 H, d, J=6.1 Hz), 1.2–1.93 (30

H, m), 2.07 (3 H, s), 2.23 (2 H, t, J= 7.1 Hz), 2.35–2.85 (2 H, m), 3.35–3.50 (1 H, m), 3.60– 3.90 (1 H, m), 3.95–4.20 (1 H, m), 3,50 (1/2 H, m), 3.57 (1/2 H, m), 5.00 (1 H, Sept, J=6.1 Hz), 5.13 (1 H, t, J=5 Hz), 6.62 (1/2 H, d, J=15 Hz), 6.68 (1/2 H, d, J=15 Hz), 7.00 (1/2 H, dd, J=10 Hz), 7.08 (1/2 H, dd, J=10 Hz, J=7.5 Hz)

Example 15

Synthesis of 7-{(1R,2R,3R,5S)-5-acetoxy-2-[(E)- 5,5-difluoro-7-methyl-oxoocto-2-enyl]-3-(tetrahydropyranyloxy) cyclopentyl} methyl heptanoate:

and the mixture was heated under reflux for 2 days. The crude product obtained after the usual work-up was purified under a silica gel column (hexane / ethyl acetate=4 / 1) to yield the subject compound, an oily material of light yellow color.

Yield: 1.11 g (80.2%)

n. m. r. (CDCl$_3$) δ: 0.99 (6 H, d, J=6.5 Hz), 1.1–2.7 (26 H, s), 2.03 (1.1/2 H, s), 2.05 (1.1/2 H, s), 2.30 (2 H, t, J=7.5 Hz), 3.45 (1 H, m), 3.66 (3 H, s), 3.60–4.50 (2 H, m), 4.45 (1/2 H, m), 4.55 (1/2 H, m), 5.08 (1 H, m), 6.58 (1/2 H, d, J=15 Hz), 6.63 (1/2 H, d, J=15 Hz), 7.25 (1/2 H, dt, J=15 Hz,

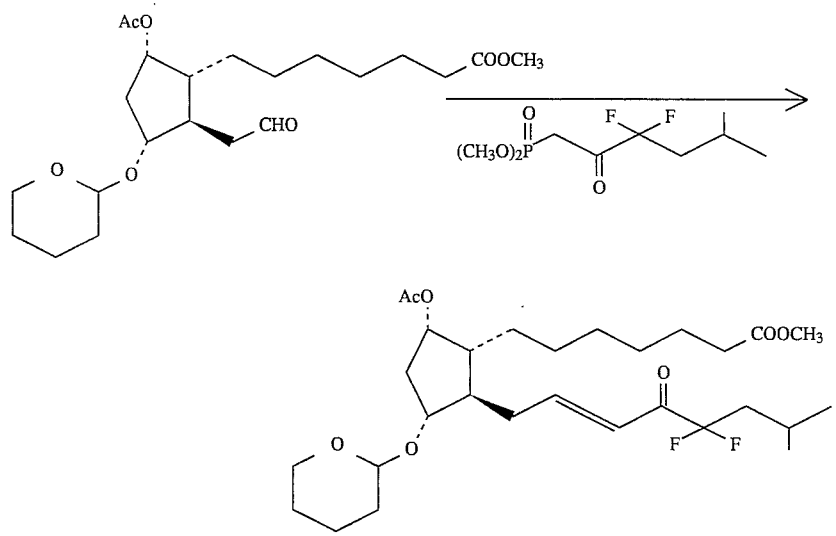

To a THF (15 ml) solution of dimethyl (3,3-difluoro-5-methyl-2-oxohexyl) phosphonate (2.15 g), kept at 0° C. was added a THF solution of t-butoxy potassium (1.0-M, 8.3 ml), and the mixture was stirred at room temperature for 1 hour. The solution was kept at 0° C., and was added with zinc chloride (1.02 g), with stirring effected at room temperature for 1 hour. Then, a THF (5 ml) solution of 7-[(1R, 2R,3R,5S)-5-acetoxy-2-(formyl methyl)-3-(tetrahydropyranyloxy) cyclopentyl] methyl heptanoate (1.05 g) was added, J=7.5 Hz), 7.30 (1/2 H, dt, J=15 Hz, J=7.5 Hz)

Example 16

Synthesis of (Z)-7-{(1R,2R,3R,5S)-5-acetoxy-2-[ (E)-4, 4-difluoro-3-oxo-4-phenylbuto-1-enyl]-3-(tetrahydropyranyloxy) cyclopentyl} hepto-5-methyl hydrochloride:

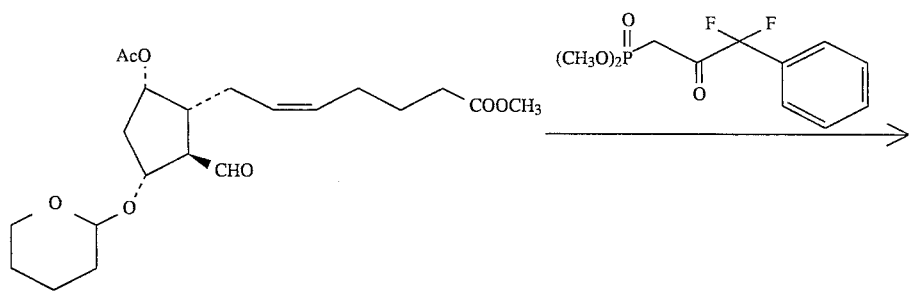

-continued

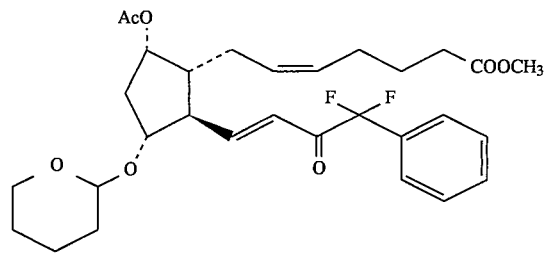

To a THF (7 ml) solution of dimethyl(3,3-difluoro- 3-phenyl-2-oxopropyl) phosphonate (1.947 g), kept at 0° C., was added a THF solution of t-butoxy potassium (1.0-M, 6.99 ml). The mixture was stirred at room temperature for 30 minutes, followed by addition of zinc chloride (0.858 g) with stirring for 1 hour. To the resultant was added a THF (7 ml) solution of (Z)-7-[ (1R,2R,3R,5S)-5-acetoxy-2-formyl- 3-(tetrahydropyranyloxy) cyclopentyl] hepto-5-methyl hydrochloride (1.366 g), and agitation was carried out at 60° C. for 64 hours. The crude product obtained after the usual work-up was purified on a silica gel column (hexane/ethyl acetate=3 / 2) to yield the subject compound, a colorless oily material.

Yield: 1.701 (90%)

n. m. r. (CDCl$_3$) δ: 1.22–2.85 (15 H, m), 2.05 (3 H, s), 2.27 (2 H, t, J=7.5 Hz), 3.18–3.60 (1.1/2, m), 3.67 (3 H, s), 3.60–3.90 (1/2 H, m), 3.90–4.15 (1 H, m), 4.36 (1/2 H, m), 4.53 (1/2 H, m), 5.07 (1 H, m), 5.15–5.45 (2 H, m), 6.61 (1/2 H, d, J=10 Hz), 6.70 (1/2 H, d, J=10 Hz), 7.04 (1/2 H, dd, J=10 Hz, J=10 Hz), 7.12 (1/2 H, dd, J=10 Hz, J=10 Hz), 7.40–7.65 (5 H, m)

Example 17

Synthesis of 7-{(1R,2R,3R,5S)-5-acetoxy-2-[ (E)-4-[(1RS)-3-methylene cyclopentyl]-4,4-difluoro-3-oxobuto-1-enyl]-3-(tetrahydropyranyloxy) cyclopentyl} methyl heptanoate:

dimethyl[3,3-difluoro-3-[(1RS)-3-methylene cyclopentyl]-2-oxopropyl] phosphonate (0.950 g). The mixture was stirred at room temperature for 30 minutes and then zinc chloride (0.417 g) was added, followed by further stirring for 1 hour. To the resultant was added a THF (3 ml) solution of 7-[(1R,2R,3R,5S)-5-acetoxyformyl- 3-(tetrahydropyranyloxy) cyclopentyl] methyl heptanoate (1.22 g), and the mixture was heated under reflux for 2 days. A phosphonate anion prepared from phosphonate 6 (0.864 g), a THF solution of t-butoxy potassium (1.0-M, 3.06 ml), and zinc chloride (0.379 g) was added, and the mixture was again heated under reflux for 3 days. The crude product obtained after the usual work-up was purified on a silica gel column (ethyl acetate/hexane=1/3) to yield the subject compound, a colorless oily material.

Yield: 1.60 g (94.1%)

n. m. r. (CDCl$_3$), δ: 1.1–1.4 (7 H, m), 1.4– 2.0 (13 H, m), 2.07 (3 H, s), 2.2–2.9 (7 H, m), 2.29 (2 H, t, J=7.5 Hz), 3.35–3.52 (1 H. m), 3.6–3.9 (1 H, m), 3.67 (3 H, s), 3.97–4.2 (1 H. m), 4.52 (1/2 H. m), 4.58 H, m), 4.88 (2 H, brs), 5.15 (1 H, t, J=5 Hz), 6.63 (1/2 H, d, J=10 Hz), 6.70 (1/2 H, d, J=10 Hz), 7.04 (1/2, dd, J=10 Hz, J=Hz), 7. (H, dd, J=10 Hz, J=10 Hz)

Example 18

Synthesis of 7-[(1R,2R,3R,5S)-2-(5,5-difluoro)- 8-methoxy-4-oxoocto-2-enyl)-5-hydroxy-3-(tetrahydropyranyloxy) cyclopentyl] methyl heptanoate:

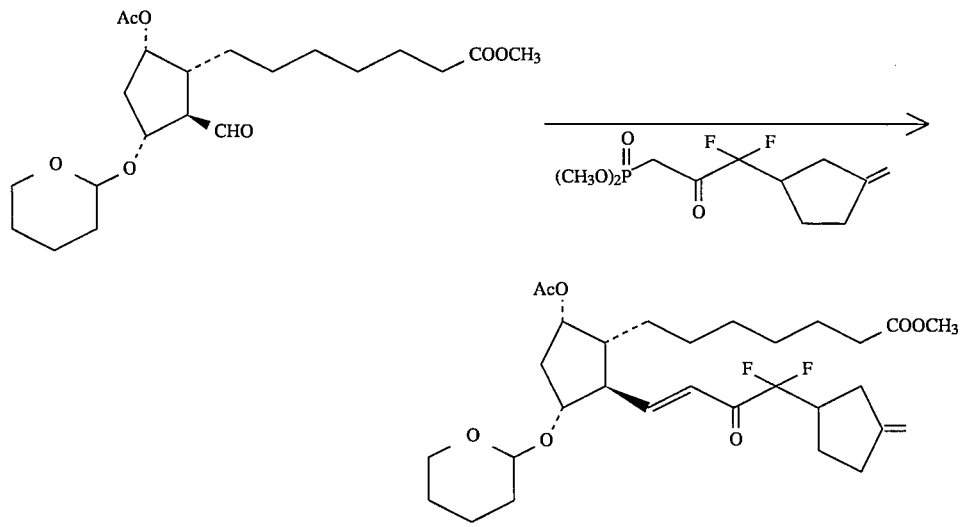

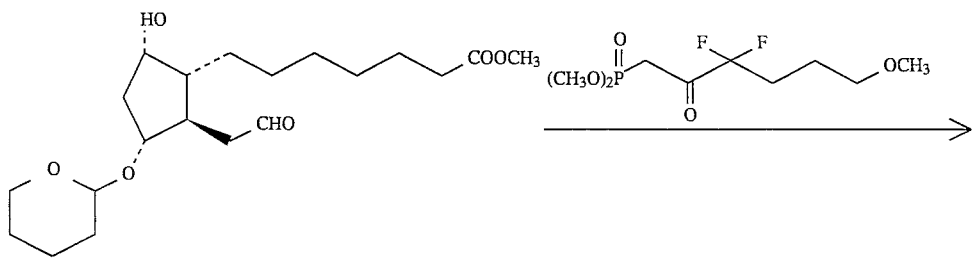

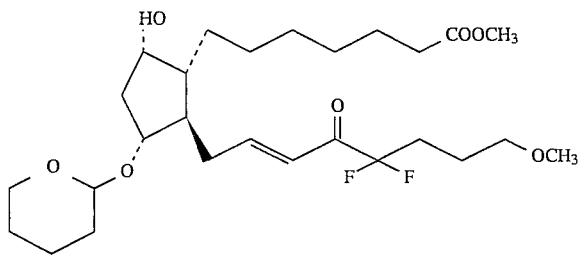

To a THF solution of t-butoxy potassium (1.0-M, 10.9 ml), kept at 0° C., was added dropwise a dry THF solution (12 ml) of dimethyl(3,3-difluoro-6-methoxy-2-oxohexyl)phosphonate (3.00 g). After the mixture was stirred at room temperature for 30 minutes, zinc anhydride (1.49 g) was added thereto, followed by stirring for 1 hour. Then, a THF (12 ml) solution of 7-[ (1R,2R,3R,5S)-2-(formyl methyl)-5-hydroxy-3-(tetrahydropyranyloxy) cyclopentyl] methyl heptanoate (1.35 g) was added, and the mixture was heated under reflux for 50 hours, followed by addition of acetic acid (0.856 ml) at 0° C. The crude product obtained after the usual work-up was chromatographed on a silica gel column (ethyl acetate/hexane=4/6) to yield the subject compound, an oily material of light yellow color.

Yield: 1.58 g (84%)

Example 19

Synthesis of (Z)-7-{(1R,2R,3R,5S)-5-acetoxy-2-[ (E)-4,4-difluoro-3-oxoocto-1-enyl]-3-(tetrahydropyranyloxy) cyclopentyl} hepto-5-methyl hydrochloride:

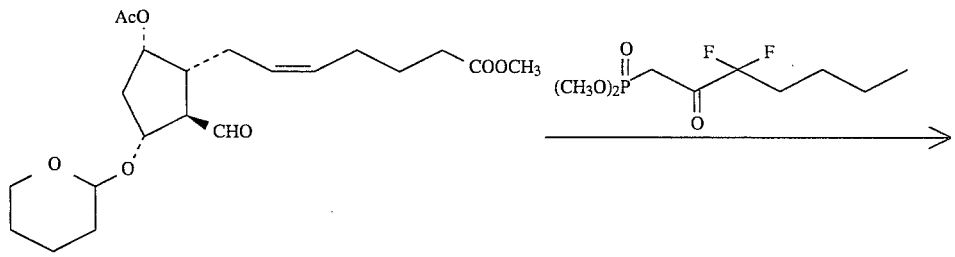

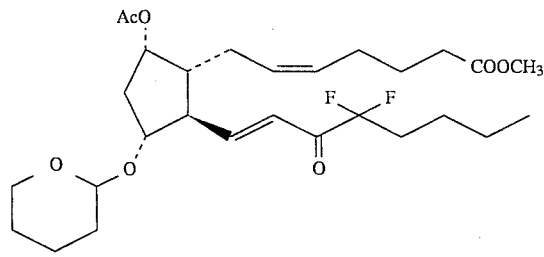

A t-butyl lithium solution (1,7-M pentane solution, 0.92 ml) was diluted with THF (1 ml) at −78 ° C., to which was added dropwise a THF (2 ml) solution of dimethyl (3,3-difluoro-2-oxoheptyl) phosphonate (0.4046 g). Stirring was carried out at room temperature for 1 hour, and then zinc chloride (0.1922 g) was added, followed by further stirring for 1 hour. To the resultant was added a THF solution (2 ml) of (Z)-7-[ (1R,2R,3R,5S)-5-acetoxy-2-formyl-3-(tetrahydropyranyloxy) cyclopentyl] hepto-5- methyl hydrochloride (0.2071 g), and the mixture was heated under reflux for 3 days. The crude product obtained after the usual work-up was purified on a silica gel column to yield the subject compound, an oily material of light yellow color.

Yield: 0.2302 g (83.3%)

n. m. r. (CDCl$_3$) δ: 0.92 (3 H, t, J=7.5 Hz), 1.2–3.9 (22 H, m), 2.06 (3 H, s.), 2.29 (2 H, t, J= 7.5 Hz), 3.35–3.50 (1 H, m), 3.66 (3 H, s), 3.60–3.90 (1 H, m), 3.95–4.20 (1 H, m), 4.51 (1/2 H, t. J=2.5Hz), 4.57 (1/2 H, t, J=2.5 Hz), 5.10 (1

H, t, J=5.0 Hz), 5.23 (2 H, m), 6.63 (1/2H, d, J=15 Hz), 6.69 (1/2 H, d, J=15 Hz), 7.06 (1/2 H, dd, J=15 Hz, J=7.5 Hz), 7.14 (1/2 H, dd, J=15 Hz, J=7.5 Hz)

Example 20

Synthesis of (Z)-7-{(1R,2R,3R,5S)-5-acetoxy-2-[ (E)-4,4-difluoro-3-oxoocto-1-enyl]-3-(tetrahydropyranyloxy)cyclopentyl} hepto-5-methyl hydrochloride:

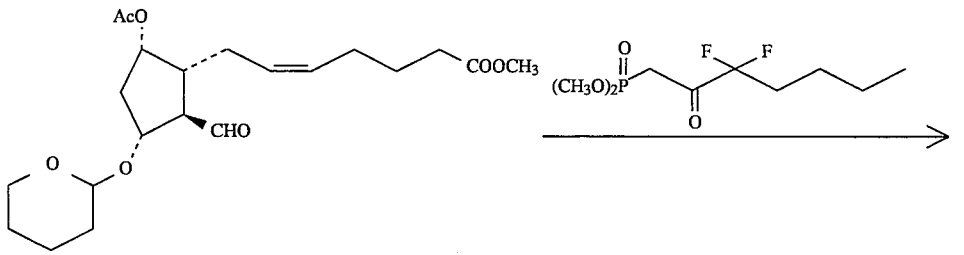

Sodium amide (0.0750 g) was suspended in THF (2 ml), into which a solution of dimethyl (3,3-difluoro-2-oxoheptyl)phosphonate (0.4965 g) in THF (2 ml)was added, followed by stirring at 50° C. for 30 minutes. To the resultant

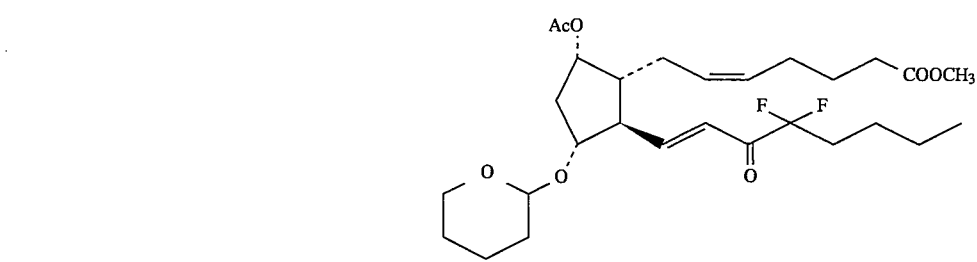

was added zinc chloride (0.2359 g) with stirring for 1 hour at room temperature. A THF (2 ml) solution of (Z)-7-[(1R,2R,3R,5S)-5-acetoxy-2-formyl-3-(tetrahydropyranyloxy)cyclopentyl] hepto-5-methyl hydrochloride (0.2540 g) was added, and the mixture was heated under reflux for 24 hours. The crude product obtained after the usual work-up purified on a silica gel column (hexane/ethyl acetate=3.5/1) to yield the subject compound, an oily material of light yellow color.

Yield: 0.1900 g (56%)

Example 21

Synthesis of (Z)-7-{(1R,2R,3R,5S)-5-acetoxy-2-[ (E)-4,4-difluoro-3-oxoocto-1-enyl]-3-(tetrahydropyranyloxy)cyclopentyl} hepto-5-methyl hydrochloride:

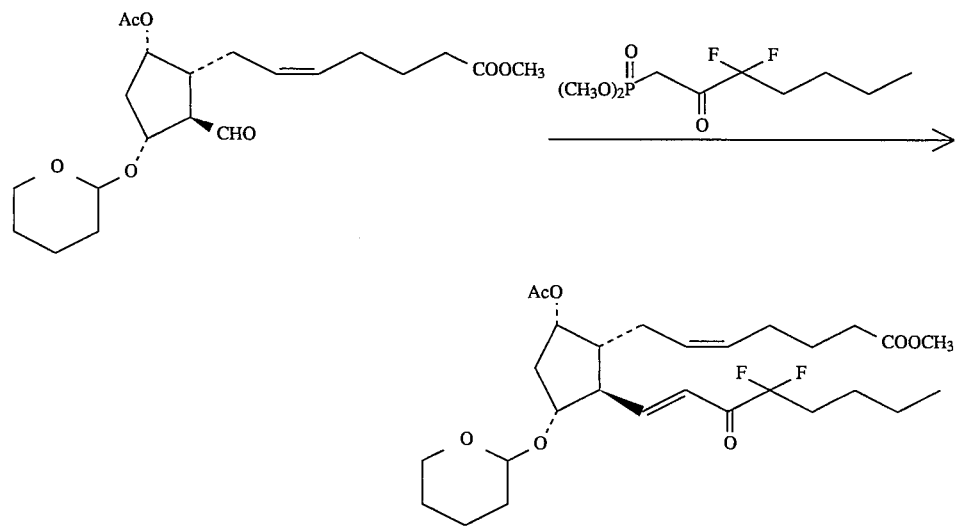

To a THF (3 ml) solution of 4 dimethylamino pyridine (0.1320 g) was added dimethyl(3,3-difluoro-2-oxoheptyl)phosphonate (0.2789 g) in THF (1.4 ml), and stirring was carried out at room temperature for 1 hour, followed by addition of zinc chloride (0.1325 g) and further stirring for 1 hour. To the resultant was added a THF (1.5 ml) solution of (Z)-7-[(1R,2R,3R,5S)-5-acetoxy- 2-formyl-3-(tetrahydropyranyloxy) cyclopentyl] hepto-5-methyl hydrochloride (0.1428 g) was added, and the mixture was heated under reflux for 3 days. The crude product obtained after the usual work-up was purified on a silica gel column (hexane/ethyl acetate=3.5/1) to yield the subject compound, an oily material of light yellow color.

Yield: 0.1172 g (61.7%)

Example 22

Synthesis of (Z)-7-{(1R,2R,3R,5S)-5-acetoxy-2-[ (E)-4, 4-difluoro-3-oxoocto-1-enyl]-3-(tetrahydropyranyloxy) cyclopentyl} hepto-5-methyl hydrochloride:

1 hour. Zinc chloride (0.1836 g) was added at room temperature with stirring for 1 hour. Then, a THF (2 ml) solution of (Z)-7-[(1R,2R,3R,5S)-5-acetoxy- 2-formyl-3-(tetrahydropyranyloxy) cyclopentyl] hepto-5-methyl hydrochloride (0.1978 g) was added, and the mixture was heated under reflux for 3 days. The crude product obtained after the usual work-up was purified on a silica gel column (hexane/ethyl acetate= 3.5/1) to yield the subject compound, an oily material of light yellow color.

Yield: 0.1634 g (61.9%)

Example 23

Synthesis of (Z)-7-{(1R,2R,3R,5S)-5-acetoxy-2-[ (E)-4, 4-difluoro-3-oxoocto-1-enyl]-3-(tetrahydropyranyloxy)

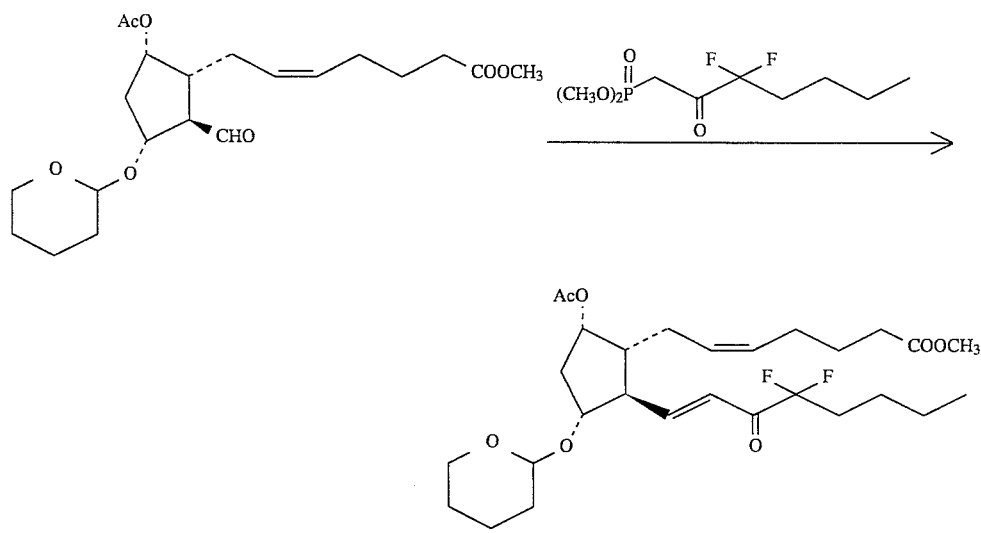

To triethylamine (0.21 ml) in THF (1 ml) was added dimethyl(3,3-difluoro-2-oxoheptyl)phosphonate (0.3865 g) in THF (2 ml), and the mixture was heated under reflux for cyclopentyl} hepto-5-methyl hydrochloride:

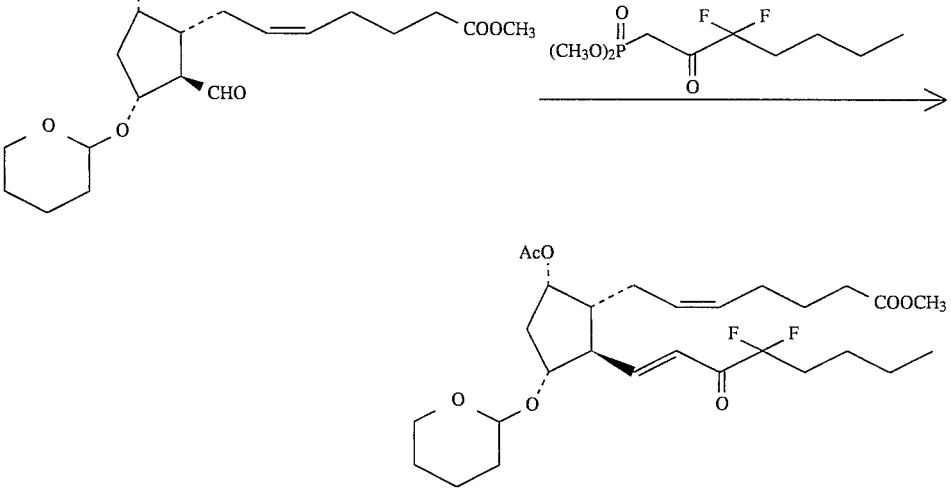

To sodium hydride (63%, 0.0353 g), washed in petroleum ether, was added DMSO (0.8 ml) with stirring at 70° C. for 1 hour, and thus sodium methylsulfinyl carbanion was obtained. A THF (2.3 ml) solution of dimethyl(3,3-difluoro-2-oxoheptyl)phosphonate (0.2324 g) was added at room temperature and the mixture was stirred for 1 hour, followed by addition of zinc chloride (0.1104 g) and further stirring for 1 hour. To the resultant was added a THF (2 ml) solution of (Z)-7-[(1R,2R,3R,5S)-5-acetoxy- 2-formyl-3-(tetrahydropyranyloxy) cyclopentyl] hepto-5-methyl hydrochloride (0.1785 g), and the mixture was heated under reflux for 24 hours. Phosphonate anion which was similarly prepared from sodium hydride (63%, 0.0174 g), DMSO (0.4 ml), phosphonate (0.1162 g) and zinc chloride (0.0502 g) was added, and the mixture was heated under reflux for 2 days for further reaction. The crude product obtained after the usual work-up was purified on a silica gel column (hexane/ethyl acetate=7/2) to yield the subject compound, an oily compound of light yellow color.

Yield: 0.1434 g (60.2%)

Example 24

Synthesis of (Z)-7-{(1R,2R,3R,5S)-5-acetoxy-2-[ (E)-4,4-difluoro-3-oxoocto-1-enyl]-3-(tetrahydropyranyloxy) cyclopentyl} hepto-5-methyl hydrochloride:

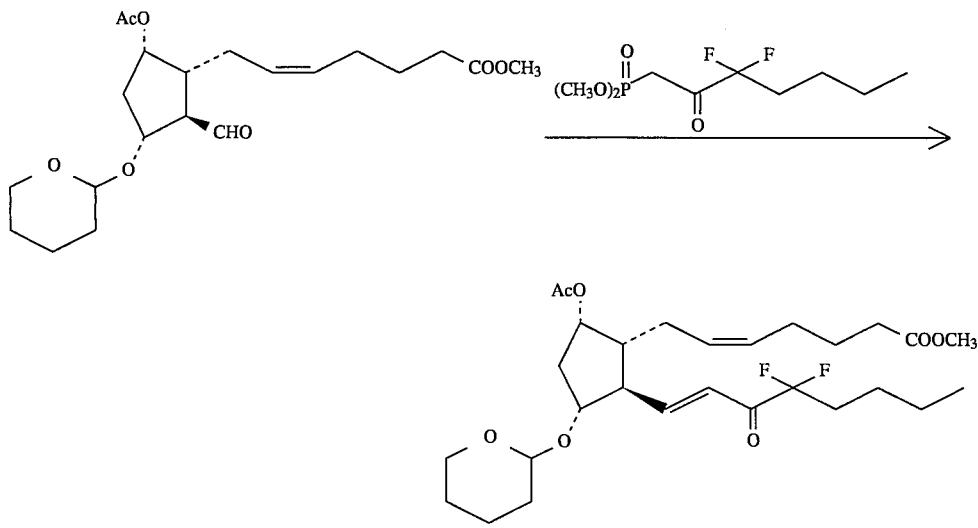

To a THF (2 ml) solution of dimethyl(3,3-difluoro- 2-oxoheptyl)phosphonate (0.3656 g), kept at 0° C., was added an aqueous solution of 1-N caustic soda (1.40 ml), followed by stirring at room temperature for 20 minutes. The mixture was concentrated as such under reduced pressure, followed by addition of toluene and concentrated under reduced pressure. The residue was dried under reduced pressure by using a vacuum pump for 1 hour, followed by addition of THF (2 ml). Further, zinc chloride (0.1713 g) was added with stirring for 1 hour. Then, a THF (2 ml) solution of (Z)-7-[(1R,2R,3R,5S)-5-acetoxy- 2-formyl-3-(tetrahydropyranyloxy) cyclopentyl] hepto-5-methyl hydrochloride (0.1870 g) was added, and the mixture was heated under reflux for 3 days. The crude product obtained after the usual work-up was purified on a silica gel column (hexane/ethyl acetate= 7/2) to yield the subject compound, an oily material of light yellow color. Yield: 0.2143 g (85.8%)

Effect of the Invention

According to the method of the present invention, a ω chain is introduced into the aldehyde in the process of synthesizing prostaglandins, particularly prostaglandins having at least one halogen atom at the 16-position or 17-position, and this provides for considerable yield improvement in the production of α,β-unsaturated ketones.

What is claimed is:

1. A method of producing an α,β-unsaturated ketone which comprises reacting an aldehyde expressed by the formula:

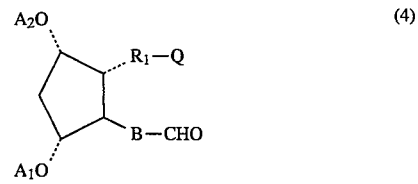

where, $A_1$ and $A_2$ represent a hydrogen atom or a hydroxyl protection group; B represents a simple bond of —$CH_2$—; $R_1$ represents a bivalent saturated or unsaturated aliphatic hydrocarbon residue having a carbon number of 1 to 10; Q represents a —COOH group or a derivative thereof; provided that -$OA_1$ and Q may form

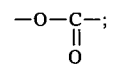

with a 2-oxoalkyl phosphonate expressed by the formula:

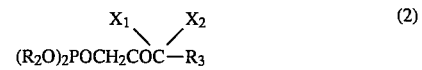

where, $X_1$ and $X_2$ represent hydrogen atom, lower alkyl group or halogen atom; $R_2$ represents a lower alkyl group; $R_3$ represents a saturated or unsaturated aliphatic hydrocarbon group having a carbon number of 1 to 10 which may have a lower alkoxy group, a saturated or unsaturated cycloalkyl group having a carbon number of 3 to 7, a saturated or unsaturated phenyl group or a saturated or unsaturated phenoxy group, the resulting α,β-unsaturated ketone bing expressed by the formula:

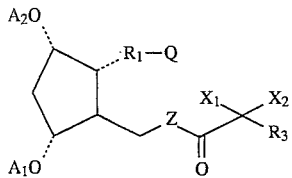

where $A_1$, $A_2$, $R_3$, $X_1$ and $X_2$ have same meanings as defined above; and Z represents =CH— or —CH=CH—, the reaction being carried out under the presence of at least one kind of base selected from the group consisting of alkali hydride, alkoxide, amide, organic alkali, sulfinylcarbonion compounds, secondary amine, tertiary amine, aromatic heterocyclic compound and alkali hydroxide, and a zinc compound.

2. A method of producing an α,β-unsaturated ketone which comprises reacting an aldehyde expressed by the formula:

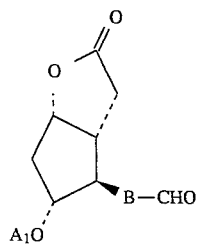

where, $A_1$ represents a hydrogen atom or a hydroxyl protection group; B represents a simple bond of —CH$_2$—; with a 2-oxoalkyl phosphonate expressed by the formula:

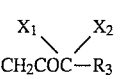

where, $X_1$ and $X_2$ represent hydrogen atom, lower alkyl group or halogen atom; $R_2$ represents a lower alkyl group; $R_3$ represents a saturated or unsaturated aliphatic hydrocarbon group having a carbon number of 1 to 10 which may have a lower alkoxy group, a saturated or unsaturated cycloalkyl group having a carbon number of 3 to 7, a saturated or unsaturated phenyl group or a saturated or unsaturated phenoxy group, the resulting α,β-unsaturated ketone being expressed by the formula:

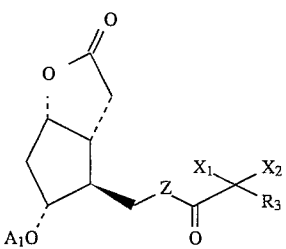

where $A_1$, $R_3$, $X_1$ and $X_2$ have same meanings as defined above; and Z represents =CH— or —CH=CH—, the reaction being carried out under the presence of at least one kind of base selected from the group consisting of alkoxide, amide, organic alkali, sulfinylcarbonion compounds, secondary amine, tertiary amine, aromatic heterocyclic compound and alkali hydroxide, and a zinc compound.

3. A method according to claim 1, wherein at least one of $X_1$ and $X_2$ is a halogen atom.

4. A method according to claim 2, wherein at least one of $X_1$ and $X_2$ is a halogen atom.

* * * * *

UNITED STATES PATENT AND TRADEMARK OFFICE
CERTIFICATE OF CORRECTION

PATENT NO.   : 5,468,880
DATED        : November 21, 1995
INVENTOR(S)  : UENO et al.

It is certified that error(s) appears in the above-identified patent and that said Letters Patent is hereby corrected as shown below:

Title page, for Item [30] under "Sep. 30, 1992 [JP] Japan.....4-261283", insert

--Sep. 29, 1993 [PCT] ................PCT/JP93/01387--.

Item [22] Filed should read "September 29, 1993" and the following should be inserted after item [22];

--item [86]  PCT No:  PCT/JP93/0138
                  371 Date: May 31, 1994
                  102(e) Date: May 31, 1994--.

--item [87]  PCT Pub. No.: WO94/07884
                  PCT Pub. Date: April 14, 1994--.

Signed and Sealed this

Eleventh Day of June, 1996

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO.   : 5,468,880
DATED        : November 21, 1995
INVENTOR(S)  : UENO et al.

It is certified that error(s) appears in the above-identified patent and that said Letters Patent is hereby corrected as shown below:

On the title page,
Item [86], change "PCT No: PCT/JP93/0138" to --PCT No: PCT/JP93/01387--

Signed and Sealed this

Seventeenth Day of September, 1996

Attest:

BRUCE LEHMAN

*Attesting Officer*   Commissioner of Patents and Trademarks